United States Patent [19]

Parsons

[11] Patent Number: 4,652,641
[45] Date of Patent: Mar. 24, 1987

[54] BENZOFUSED LACTAMS USEFUL AS ANTIHYPERTENSIVE AGENTS AND AS CHOLECYSTOKININ ANTAGONISTS

[75] Inventor: William H. Parsons, Rahway, N.J.
[73] Assignee: S. C. Mitri, Rahway, N.J.
[21] Appl. No.: 810,118
[22] Filed: Dec. 18, 1985

Related U.S. Application Data

[63] Continuation of Ser. No. 624,855, Jun. 26, 1984, abandoned.

[51] Int. Cl.$^4$ ............... C07D 223/16; C07D 215/16; C07D 217/04
[52] U.S. Cl. ............................. 540/523; 546/157; 546/146
[58] Field of Search ............... 260/239.3 B; 546/157, 546/146; 514/312, 213; 540/523

[56] References Cited

U.S. PATENT DOCUMENTS 2,991,286  7/1961  Corson et al. .................. 540/523

*Primary Examiner*—Robert T. Bond
*Attorney, Agent, or Firm*—S. C. Mitri; M. C. Sudol; M. A. Monaco

[57] ABSTRACT

Compounds of the formula:

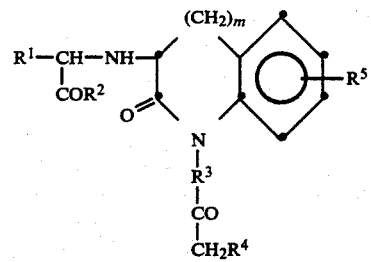

and pharmaceutically acceptable salts thereof are inhibitors of angiotensin I converting enzyme and are useful as antihypertensive agents and are also useful as cholecystokinin antagonists.

3 Claims, No Drawings

BENZOFUSED LACTAMS USEFUL AS ANTIHYPERTENSIVE AGENTS AND AS CHOLECYSTOKININ ANTAGONISTS

This is a continuation of application Ser. No. 624,855, filed June 26, 1984, now abandoned.

BACKGROUND OF THE INVENTION

The present invention is concerned with novel benzofused lactams which are effective inhibitors of angiotensin I converting enzyme and effective antagonists of cholecystokinin. These novel compounds are, consequently, combined with pharmaceutically acceptable carriers to form pharmaceutical compositions of the present invention and are used in a method of treating hypertension, gastrointestinal disorders, central nervous system disorders, or regulating appetite in humans.

Angiotensin II, a powerful vasoconstrictor hormonal peptide, is formed from the inactive angiotensin I by the action of angiotensin converting enzyme (ACE). Recently, potent inhibitors of ACE have been reported which are capable of lowering the blood pressure in hypertensive patients. The novel benzofused lactams of the present invention are also potent inhibitors of ACE.

Cholecystokinin (CCK) is a neuropeptide composed of thirty-three aminoacids. See: Mutt and Jorpes, *Biochem. J.* 125 678 (1971). The carboxyl terminal octapeptide (CCK-8) also occurs naturally and is fully active. CCK exists in both gastrointestinal tissue and the central nervous system. V. Mutt, *Gastrointestinal Hormones*, G. B. J. Glass, Ed., Raven Press, N.Y., (1980) p. 169. CCK is believed to play an important role in appetite regulation and CCK may be a physiological satiety hormone. G. P. Smith, *Eating and Its Disorders*, A. J. Stunkard and E. Stellar, Eds, Raven Press, New York, 1984, p. 67.

Among additional effects of CCK are stimulation of colonic motility, stimulation of gall bladder contraction, stimulation of pancreatic enzyme secretion, and inhibition of gastric emptying. CCK reportedly co-exists with dopamine in certain mid-brain neurons and thus may also play a role in the functioning of dopaminergic systems in the brain as well as serving as a neurotransmitter in its own right. See: A. J. Prange et al., "Peptides in the Central Nervous System", *Ann. Repts. Med. Chem.* 17 31, 33 (1982) and references cited therein; J. A. Williams, *Biomed. Res.* 3 107 (1982); and J. E. Morley, *Life Sci.* 30, 479 (1982).

CCK antagonists are useful in the treatment and prevention of CCK-related disorders of the gastrointestinal, central nervous and appetite regulatory systems of animals, especially humans. Three distinct chemical classes of CCK receptor antagonists have been reported. One class comprises derivatives of cyclic nucleotides; detailed structure-function studies have demonstrated that of the various members of this class, dibutyryl cyclic GMP is the most potent. See; N. Barlos et al., *Am. J. Physiol.*, 242, G161 (1982) and P. Robberecht et al., *Mol. Pharmacol.*, 17, 268 (1980). The second class comprises peptide antagonists which are C-terminal fragments and analogs of CCK. Recent structure-function studies have shown that both shorter C-terminal fragments of CCK (Boc-Met-Asp-Phe-NH$_2$, Met-Asp-Phe-NH$_2$) as well as longer CCK fragments (Cbz-Tyr(-SO$_3$H)-Met-Gly-Trp-Met-Asp-NH$_2$) can function as CCK antagonists. See: R. T. Jensen et al., *Biochim. Biophys. Acta*, 757, 250 (1983) and M. Spanarkel et al., *J. Biol. Chem.*, 258, 6746 (1983). The third class of CCK receptor antagonists comprises the amino acid derivatives; proglumide, a derivative of glutaramic acid, and the N-acyl tryptophans including para-chlorobenzoyl-L-tryptophan (benzotript). See W. F. Hahne et al., *Proc. Natl. Acad. Sci. U.S.A.*, 78, 6304 (1981) and R. T. Jensen et al., *Biochem. Biophys. Acta.*, 761, 269 (1983). All of these compounds are relatively weak antagonists of CCK (IC$_{50}$: $10^{-4}$–$10^{-6}$M).

SUMMARY OF THE INVENTION

It has now been found that the compounds of this invention are inhibitors of angiotensin converting enzyme (ACE) and certain of these compounds are antagonists of cholecystokinin (CCK). Thus, these compounds are useful in the treatment of hypertension and some are useful in the treatment and prevention of CCK-related disorders of the gastrointestinal, central nervous and appetite regulatory systems of animals, especially humans.

DETAILED DESCRIPTION OF THE INVENTION

In its broadest aspect, the present invention relates to novel benzofused lactams of the formula:

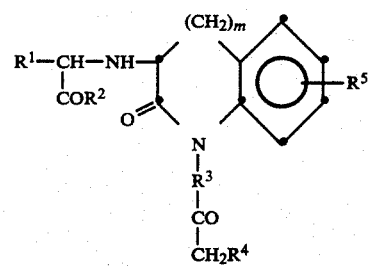

wherein:
R$^1$ is
  hydrogen;
  hydrocarbon of from 1 to 12 carbon atoms which include branched and unsaturated alkyl groups;
  C$_3$–C$_{10}$cycloalkyl;
  substituted loweralkyl wherein the substituent can be halo, hydroxy, carboxy, loweralkylthio, loweralkoxy, loweralkoxycarbonyl, carboxamido, loweraralkoxycarbonyl, amino, loweralkylamino, lowerdialkylamino, or acylamino;
  substituted loweralkyl having the formula R$_A$$^1$(CH$_2$)$_p$—Q—(CH$_2$)$_q$ wherein p is 0–2, q is 1–3, R$_A$$^1$ is aryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, N—R$_B$$^1$, CONR$_C$$^1$, NR$_C$$^1$CO, CH=CH wherein Rhd B$^1$ is hydrogen, loweralkyl, aryl, aralkyl, loweralkanoyl, or aroyl, and R$_C$$^1$ is hydrogen, or loweralkyl;
  aryl;
  substituted aryl wherein the substituent is loweralkyl, aminoloweralkyl, loweralkoxy, aryloxy, aroyl, hydroxy, halo, or dihalo; aralkyl or heteroaralkyl which include branched loweralkyl groups; substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxyloweralkyl, trihaloloweralkyl, nitro, cyano, or sulfonamido;

$R^2$ is hydroxy; loweralkoxy; loweralkenyloxy; arylloweralkoxy; acylloweralkoxy; amino; loweralkylamino; diloweralkylamino; arylalkylamino; arylamino; carboxyloweralkylamino; carboxamidoloweralkylamino; or aryloxy, or mono- or di-substituted aryloxy wherein the substituents are halo; m is 1-3;

$R^3$ is loweralkyl or substituted loweralkyl wherein the substituents are hydrogen, loweralkyl, or aryl;

$R^4$ is hydroxy; loweralkanoyloxy; arloweralkanoyloxy;

$R^5$ is hydrogen; halo; hydroxy; loweralkyl; or loweralkoxy; and a pharmaceutically acceptable salt thereof.

The loweralkyl substituents recited above represent, except where otherwise indicated, any of the variables of straight, branched, and unsaturated chain hydrocarbon radicals of from one to six carbon atoms, such as methyl, ethyl, n-propyl, i-propyl, n-butyl, i-butyl, t-butyl, n-pentyl, i-pentyl, n-hexyl; or vinyl, allyl, butenyl, and the like.

The loweralkoxy substituent represents a loweralkyl group as described above attached through an oxygen bridge.

The aralkyl and heteroaralkyl substituents recited above represent aryl or heteroaryl groups as herein defined attached through a straight or branched chain hydrocarbon of from one to six carbon atoms, for example, benzyl, phenethyl, 3,3-diphenylpropyl, 3-indolylmethyl, and the like.

Halo means chloro, bromo, iodo, or fluoro.

The aryl substituent represents phenyl, naphthyl, or biphenyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl; as well as any bicyclic group in which any of the above heterocyclic rings is fused to a benzene ring, for example, indolyl, quinolinyl, isoquinolinyl, benzimidazolyl, benzothiazolyl, and benzthienyl.

The acylamino substituent represents loweralkanoylamino and aroylamino, such as acetylamino and benzoylamino.

The Formula I compounds can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfoate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine and N-methyl-D-glucamine, and salts with amino acids such as arginine, lysine, and so forth. Water or oil-soluble or dispersible products are thereby obtained.

In the compounds of Formula I, the carbon atom to which $R^1$ is attached, as well as the carbon atoms of the $R^3$ substituent, may be asymmetric. These compounds accordingly exist in diastereoisomeric forms or in mixtures thereof. Although the L- or S- configuration is preferred for each of the asymmetric carbon atoms, diastereomers containing D- or R- amino acids have activity dependent upon their structures and have advantages with respect to metabolic stability and can, therefore, be utilized in mixture or as pure diastereomeric compounds.

Preferred compounds of the present invention are those of Formula I wherein:

$R^1$ and $R^5$ are as defined above;

$R^2$ is amino, loweralkylamino; diloweralkylamino; arylalkylamino, arylamino, hydroxy, loweralkoxy, carboxyloweralkylamino, carboxamidoloweralkylamino;

$R^3$ is methylene or ethylene;

$R^4$ is hydroxy; alkanoyloxy; arloweralkanoyloxy; and, m is 1, 2, or 3.

The compounds of this invention inhibit angiotensin converting enzyme (ACE) and thus block conversion of the decapeptide angiotensin I to angiotensin II. Angiotensin II is a potent pressor substance. Thus blood pressure lowering can result from inhibition of its biosynthesis especially in animals and humans whose hypertension is angiotensin II related. Furthermore, converting enzyme degrades the vasodilator peptide, bradykinin. Therefore, inhibitors of ACE may lower blood pressure also by potentiation of bradykinin. Although the relative importance of these and other possible mechanisms remains to be established, inhibitors of ACE are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.*, 125, 96 (1967).

Thus, the compounds of the invention are useful in treating hypertension. They are also of value in the management of acute and chronic congestive heart failure, in the treatment of secondary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

An embodiment of this invention is the use of the compounds of Formula I for the treatment and the prevention of disorders of the gastrointestinal, central nervous, and appetite regulatory systems of mammals, especially of man. Specifically, these Formula I compounds are useful in treatment and prevention of disorders of gastric acid secretion, gastrointestinal motility, pancreatic secretions, and dopaminergic functions. The compounds of Formula I are especially useful in the prevention and treatment of irritable bowel syndrome.

The ability of the compounds of Formula I to antagonize CCK and gastrin makes these compounds especially useful in the treatment and prevention of disease states wherein CCK or gastrin may be involved, for example, gastrointestinal disorders such as irritable bowel syndrome, ulcers, excess pancreatic or gastric secretion, acute pancreatis, motility disorders, central nervous system disorders caused by CCK's interaction with dopamine such as neuroleptic disorders, tardive, dyskinesia, Parkinson's disease, psychosis or Gilles de la Tourette Syndrome, and disorders of appetite regulatory systems.

CCK In Vitro Activity of Formula I Compounds

The CCK biological activity of the compounds of Formula I have been evaluated using an $^{125}$I-CCK receptor binding assay and in vitro isolated tissue preparations.

Materials and Methods

1. CCK Receptor Binding (Pancreas)

CCK-33 was radiolabeled with $^{125}$I-Bolton Hunter reagent (2000 Ci/mmole) as described by Sankara et al. (J. Biol. Chem. 254: 9349–9351, 1979). Receptor binding was performed according to Innis and Snyder (Proc. Natl. Acad. Sci. 77: 6917–6921, 1980) with the minor modification of adding the additional protease inhibitors, phenylmethane sulfonyl fluoride and o-phenanthroline. The latter two compounds have no effect on the $^{125}$I-CCK receptor binding assay.

Male Sprague-Dawley rats (200–350 g) were sacrificed by decapitation. The whole pancreas was dissected free of fat tissue and was homogenized in 20 volumes of ice-cold 50 mM, Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothriethel, 0.1 mM bacitracin, 1.2 mM phenylmethane sulfonyl fluoride and 0.5 mM o-phenanthroline). For the binding assay, 25 μl of buffer (for total binding) or unlabeled CCK-8 sulfate to give a final concentration of 1 μM (for nonspecific binding) or the compounds of Formula I (for determination inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000.

2. CCK Receptor Binding (Brain)

CCK-33 was radiolabeled and the binding was performed according to the description for the pancreas method with modifications according to the Saito, et al. (J. Neurochem. 37, 483–490 (1981)).

Male Hartley guinea pigs (300–500 g) were sacrificed by decapitation and the brains were removed and placed in ice-cold 50 mM, Tris HCl plus 7.58 g/L Trizma-7.4 (pH 7.4 at 25° C.) Cerebral cortex was dissected and used as a receptor source. Each gram of fresh guinea pig brain tissue was homogenized in 10 ml of Tris/Trizma buffer with a Brinkman polytron PT-10. The homogenates were centrifuged at 42,000 g for 15 min. Pellets were resuspended in Tris Buffer, centrifuged as above and resuspended in 200 volumes of binding assay buffer (10 mM HEPES, pH 7.7 at 25° C., 5 mM MgCl$_2$, 1 mM EGTA 0.4% BSA (bovine serum albumin), and 0.25 mg/ml bacitracin). For the binding assay, 25 μl of buffer (for total binding) or unlabeled CCK-8 sulfate to give a final concentration of 1 μM (for nonspecific binding) or the compounds of Formula I (for determination inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

In Vitro Results

1. Effect of The Compounds of Formula I on $^{125}$I-CCK-33 receptor binding Compounds of Formula I inhibited specific $^{125}$I-CCK-33 binding in a concentration dependent manner with an IC$_{50}$ less than or equal to 100 μM such as, for example:

1-(3-acetoxy-2-oxopropyl)-3-(1-carboethoxy-3-phenyl-1-propyl)aminohomodihydrocarbostyril, IC$_{50}$=25 μM.

Thus, in accordance with the present invention there is provided a pharmaceutical composition for treating hypertension or as cholecystokinin antagonists comprising a pharmaceutically acceptable carrier and a pharmaceutically effective amount of a compound of Formula I.

There is also provided, in accordance with the present invention, a method of treating hypertension or a method of treating gastrointestinal disorders, central nervous system disorders, or regulating appetite which comprises administering to a patient in need of such treatment a pharmaceutically effective amount of a compound of Formula I.

For administration, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the compounds of the invention.

The present compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetanol,
  (d) a condensation product of ethylene oxide with a partial ester derived from a fatty acid and a hexitol such as polyoxyethylene sorbitol monooleate, or
  (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturallyoccurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compositions of the invention are employed.

Treatment dosage for human beings can be varied as necessary. Generally, daily dosages of the compounds of the invention can range from about 0.5 mg to about 1000 mg; preferably, from about 5 mg to about 500 mg, whether administered as an ACE inhibitor or as a CCK antagonist.

The amount of active ingredient that may be combined with the carrier materials to produce a single dosage form will vary depending upon the host treated and the particular mode of administration. For example, a formulation intended for oral administration may contain from 5 mg to 500 gm of active agent compounded with an appropriate and convenient amount of carrier material which may vary from about 5 to about 95 percent of the total composition.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of this invention when used to treat hypertension can also be administered in combination with other antihypertensives and/or diuretics and/or calcium entry blockers. For example, the compounds of this invention can be given in combination with such compounds as acetazolamide, amiloride, aminophylline, atenolol, bendroflumethiazide, benzthiazide, bumetanide, chlorothalidone, chlorothiazide, clonidine, cryptenamine acetates and cryptenamine tannates, cyclothiazide, deserpidine, diazoxide, diltiazem, (S)-1-[[2-(3,4-dimethoxyphenyl)ethyl]amino]-3-[[4-(2-thienyl)-1H-imidazol-2-yl]-phenoxy]-2-propanol, ethacrynic acid, flumethiazide, furosemide, guanethidene sulfate, hydralazine hydrochloride, hydrochlorothiazaide, hydroflumethiazide, (+)-4-[3-[-[2-(1-hydroxycyclohexyl)ethyl]-4-oxo-2-thiazolidinyl]propyl]-benzoic acid, indacrinone and variable ratios of its enantiomers, merethoxylline procaine, methylclothiazide, methyldopa, methyldopate hydrochloride, metolazone, metoprolol tartate, minoxidil, naldolol, nifedipine, pargyline hydrochloride, pindolol, polythiazide, prazosin, propranolol, quinethazone, Rauwolfia serpentina, rescinnamine, reserpine, sodium ethacrynate, sodium nitroprusside, spironolactone, ticrynafen, timolol, triamterene, trichlormethiazide, trimethophan camsylate, bepridil, diltiazim, etafenone, falipamil, felodipine, flunarizine, gallopamil, indapamide, lidoflazine, nicardipine, nifedipine, nimopidine, nitrendipine, perhexiline, prenylamine, tiapamil, verapamil, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective in the 5 to 500 mg per day range can be effectively combined with the following compounds at the indicated per day dose range: hydrochlorothiazide (10–100 mg); chlorothiazide (125–2000 mg); manipulated indacrinone enantiomer ratio (25–150 mg); ethacrynic acid (15–2000 mg); amiloride (5–20 mg); furosemide (5–80 mg); propranolol (20–480 mg); timolol (5–60 mg); and methyldopa (65–2000 mg); and the pivaloyloxyethyl ester of methyldopa (30–1000 mg). In addition, triple drug combinations of hydrochlorothiazide (10–100 mg) plus amiloride (5–20 mg) plus converting enzyme inhibitor of this invention (5–500 mg); hydrochlorothiazide (10–100 mg) plus timolol (5–60 mg) plus the converting enzyme inhibitor of this invention (5–500 mg); or manipulated indacrinone enantiomer ratio (25–150 mg) plus amiloride (5–20 mg) plus converting enzyme inhibitor of this invention (5–500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

The compounds of Formula I can be prepared by the method shown in the following Reaction Scheme wherein $R^1$–$R^5$ and m are as defined above unless otherwise indicated.

As will be evident to those skilled in the art and as demonstrated in the Examples hereinafter, reactive groups not involved in the reactions, such as amino, carboxy, mercapto, etc., may be protected by methods standard in peptide chemistry prior to the coupling reactions and subsequently deprotected to obtain the desired products.

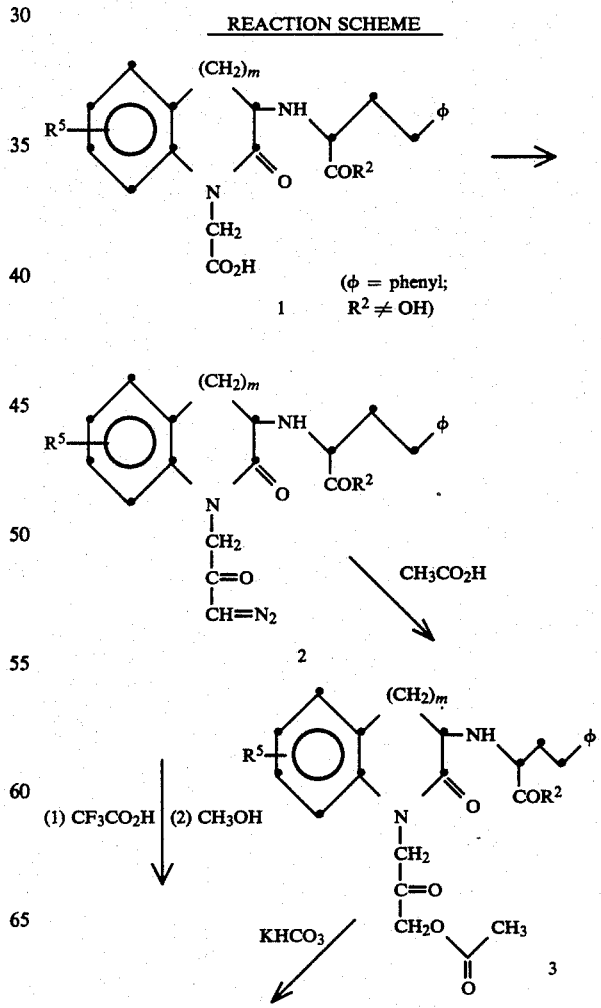

-continued
REACTION SCHEME

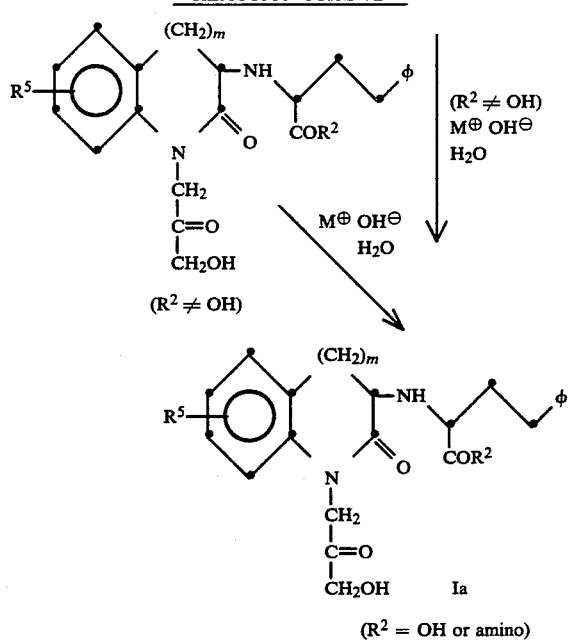

As shown in the above Reaction Scheme, benzolactam mono acid 1 [prepared according to the procedures disclosed in U.S. Pat. No. 4,410,520] can be reacted with an alkoxy chloro formate (such as ethyl or methyl chloro formate) and a tertiary amine (such as triethylamine) in an aprotic solvent (such as tetrahydrofuran (THF) to give, upon filtration, a mixed anhydride intermediate which is then reacted with an excess of diazomethane in ether to give diazomethylketone 2. Reaction of 2 in boiling acetic acid produces acetate 3 which, upon treatment with a metal hydroxide (such as sodium or lithium hydroxide), in a protic solvent (such as methanol and water) affords hydroxy methylketone acid Ia.

Alternatively, diazomethylketone 2 can be stirred in trifluoroacetic acid (TFA) followed by stirring in methanol or ethanol to give hydroxymethylketone ester 4.

Reaction of 4 with sodium hydroxide and water in a protic solvent (such as ethanol) provides a compound Ia of the invention.

Hydroxyketone ester 4 can also be prepared from acetate 3 by treating 3 with potassium or sodium bicarbonate in water.

In the above preparation, the keto acid or ester can be represented by the formula

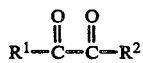

and may be, for example, 2-oxo-4-phenyl-butyric acid. Other α-keto acids or esters may be utilized to prepare other compounds of the present invention for various definitions of $R^1$ and $R^2$ Such α-keto acids are readily available or may be prepared by well-known techniques. For example, synthons such as

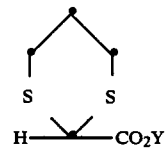

can be converted to α-keto acids or esters using methods involving alkylation followed by hydrolysis as described in the literature. An excellent method involves the reaction of Grignard reagents $R_1MgX$ with $ClCOC_2Y$ or $YO_2CCO_2Y$. Another method involves condensing substituted acetic acid esters with diethyl oxalate followed by hydrolytic decarboxylation under acidic conditions to obtain α-keto acids. Carefully controlled acid hydrolysis in alcohol of acyl cyanides, which are prepared from acid chlorides and cuprous cyanide, also proves to be a viable synthetic route to α-keto esters. Nucleophilic displacement reactions on chloro or bromo pyruvic acid (ester) can also be used to produce a variety of interesting α-keto acids (esters). In these formulae, Y is a group such as loweralkyl or benzyl and protecting groups are employed as necessary in the $R_1$ group if an interfering functionality is present.

Additional compounds of Formula I can be prepared by employing the keto acids and esters listed in Table I below.

TABLE I

Keto Acids and Esters of the Formula $\begin{matrix} R^1-C=O \\ | \\ COOR \end{matrix}$ (II.)

(a) ⬡—CH$_2$CH$_2$COCOOH (b) ⬡—CH$_2$CH$_2$COCOOC$_2$H$_5$ (c) ⬡—CH$_2$CH$_2$COCOOCH$_2$C$_6$H$_5$ (d) ⬡—CH$_2$CH$_2$CH$_2$COCOOC$_2$H$_5$ (e) Cl—⬡—CH$_2$COCOOH (f) indole-CH$_2$CH$_2$COCOOC$_2$H$_5$

TABLE I-continued

Keto Acids and Esters of the Formula $\overset{R^1-C=O}{\underset{COOR}{|}}$ (II.)

(g) [thiophene]—CH₂CH₂COCOOH (h) [pyridine]—CH₂CH₂COCOOC₂H₅

(i) [quinoline]—CH₂CH₂COCOOH (j) HO—[phenyl]—CH₂CH₂COCOOH (k) Cl—[phenyl]—CH₂CH₂COCOOH (l) O₂N—[phenyl]—CH₂CH₂COCOOC₂H₅
(precursor for the corresponding amino compound)

(m) CH₂NH—CBZ—[phenyl]—CH₂CH₂COCOOH
(precursor for the corresponding amino compound)

(n) [phenyl]—O—CH₂COCOOC₂H₅

(o) [phenyl]—S—CH₂COCOOC₂H₅

(p) CH₃S—CH₂CH₂COCOOH
(q) (CH₃)₂—CH₂CH₂COCOOH
(r) CBZ—HN(CH₂)₄—COCOOH
(precursor for the corresponding amino compound)

TABLE I-continued

Keto Acids and Esters of the Formula $\overset{R^1-C=O}{\underset{COOR}{|}}$ (II.)

(s) [phenyl]—CH₂—COCOOH (t) HO—[phenyl]—CH₂—COCOOH (u) [indole]—CH₂—COCOOH

The following examples set forth the best mode currently known for preparing the compounds of the invention and are not intended to be construed as limitative, but illustrative, thereof. Unless otherwise indicated, all temperatures are in degrees Celcius.

EXAMPLE 1

1-(3-Diazo-2-oxo-1-propyl)-3-(1-carboethoxy-3-phenylpropyl)amino homodihydrocarbostyril

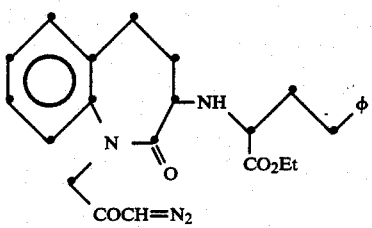

To a solution of 0.5 gm of 1-carboxymethyl3-(1-carboethoxy-3-phenyl-propyl)amino homodihydrocarbostyril (racemate no. 2) in 5 mL of THF at 0° C. there was added with stirring 0.167 mL of triethylamine followed by 0.097 mL of methyl chloro formate. Stirring at 0° C. was continued for 15 minutes whereupon the reaction mixture was filtered in a nitrogen atmosphere to remove the precipitated triethylamine hydrochloride. To the remaining solution at 0° C. there was then added a solution of freshly prepared diazomethane in ether. The solution was then stirred 12 hours at 0° C. The reaction's progress was monitored by TLC (silica, 1:1 hexanes: ethylacetate) and diazomethane solution was added as needed. When the reaction was complete, the solution was filtered and the solvents removed at reduced pressure. The crude reaction product was purified by chromatography, (silica, 1:1, hexanes:ethylacetate) to give 0.470 gm of diazoketone 1.87% TLC (2:1, ethylacetate:hexanes) $R_f$=0.50, NMR (CDCl₃, TMS) 1.21 (t, 3H); 1.8–2.8 (m, 8H); 3.0–3.4 (m, 3H); 4.1 (q, 2H); 4.42 (q, 2H); 5.58 (s, 1H); 7.06 (2s, 9H).

EXAMPLE 2

1-(3-Acetoxy-2-oxopropyl)-3-(1-carboethoxy-3-phenyl-propyl)amino homodihydrocarbostyril

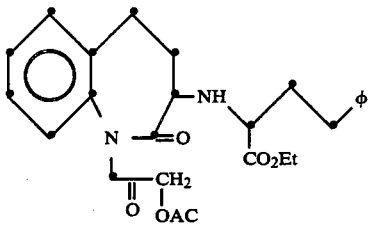

A solution of 0.3 gms of the diazoketone (2) from Example 1 in 5 mL of Acetic acid was refluxed for 1 hour at which time the acetic acid was removed in vacuo. The crude product was chromatographed (silica, 3:1, ethylacetate:hexanes) to give 0.25 gm of the title compound.

TLC (silica, ethylacetate) $R_f$=0.73

An. Calc. for $C_{27}H_{32}N_2O_6$: N, 5.83; C, 67.48; H, 6.71. Found: N, 5.60; C, 67.19; H, 6.73.

NMR (CDCl$_3$, TMS) 1.2 (t, 3H), 1.7–3.0 (m, 7H); 2.2 (s, 3H); 3.0–3.6 (m, 3H); 4.0 (q, 2H); 3.8–4.2 (m, 1H); 4.6 (s, 2H); 4.8 (s, 2H); 7.2 (s, 9H).

EXAMPLE 3

1-(3-Hydroxy-2-oxopropyl)-3-(1-carboethoxy-3-phenylpropyl)amino homodihydrocarbostyril

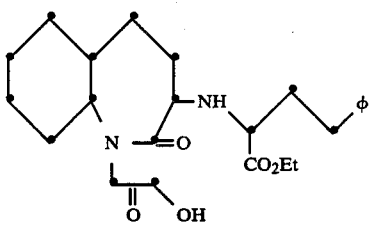

A solution of 1.2 gm of the diazoketone 2 from Example 1 in 10 mL of trifluoroacetic acid was stirred at room temperature for 3 hours at which time the solvent was removed at reduced pressure. The crude reaction mixture was dissolved in 10 mL of methanol and the solution stirred 6 hours at room temperature whereupon the methanol was removed in vacuo. The crude product was chromatographed (silica, ethylacetate) to give 0.7 gm of the title of product.

TLC (silica, ethylacetate) $R_f$=0.58.

NMR (CDCl$_3$, TMS): 1.1 (t, 3H); 1.6–3.0 (m, 6H); 3.0–3.15 (m, 3H); 4.0 (q,2H); 4.0–4.3 (m, 1H); 4.3 (s, 2H); 4.6 (s, 2H); 7.1 (s, 9H).

EXAMPLE 4

1-(3-Hydroxy-2-oxopropyl)-3-(1-carboxy-3-phenyl propyl)amino homodihydrocarbostyril

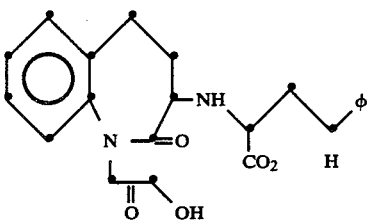

To a solution of 0.075 gm of the compound from Example 3 in 0.3 mL of methanol and 0.266 mL of a 3N solution of sodium hydroxide was stirred for 12 hours at room temperature. The H$_2$O and methanol was evaporated at reduced pressure. The crude product was dissolved in 1 mL of H$_2$O and carefully acidified with acetic acid. A white solid precipitated upon trituration, and, upon filtration and drying in vacuo, 40 mg (59%) of the titled product was isolated.

TLC (silica, 85:85:15 ethanol:methylene chloride:ammonium hydroxide) $R_f$=0.45.

An. Calc. for $C_{23}H_{26}N_2O_5.1\frac{3}{4}$ H$_2$O: N, 6.34; C, 62.52; H, 5.93. Found: N, 6.36; C, 62.56; H, 6.05.

NMR (D$_2$, NaOD) 1.6–3.0 (m, 6H); 3.0–3.5 (m, 3H); 3.9–4.5 (m, 5H); 7.1 (bs, 9H).

What is claimed is:

1. A compound of the formula:

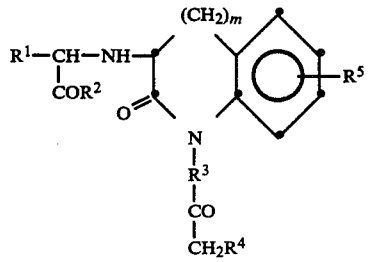

wherein:

R$^1$ is hydrogen;

straight chain or branched, saturated or unsaturated hydrocarbon of 1 to 12 carbon atoms;

C$_3$–C$_{10}$ cycloalkyl;

substituted C$_1$–C$_6$alkyl wherein the substituent can be halo, hydroxy, carboxy, C$_1$–C$_6$alkylthio, C$_1$–C$_6$alkoxy, C$_1$–C$_6$alkoxycarbonyl, carboxamido, aryl-C$_1$–C$_6$–C$_6$-alkoxycarbonyl, amino, C$_1$–C$_6$alkylamino, di-C$_1$–C$_6$-alkylamino, C$_1$–C$_6$alkanoylamino, or aroylamino;

substituted C$_1$–C$_6$alkyl having the formula R$_A{}^1$(CH$_2$)$_p$—Q—(CH$_2$)$_q$ wherein p is 0–2, q is 1–3, R$_A{}^1$ is aryl or heteroaryl optionally substituted by amino, di-C$_1$–C$_6$-alkylamino, C$_1$–C$_6$alkylamino, hydroxy, hydroxy-C$_1$–C$_6$-alkyl, amino-C$_1$–C$_6$-alkyl, thihalo-C$_1$–C$_6$-alkyl, cyano, nitro, sulfonamido, aroyl, C$_1$–C$_6$alkyl, halo, dihalo, and C$_1$–C$_6$alkoxy, and Q is O, S, N-R$_B{}^1$, CONR$_C{}^1$, NR$_C{}^1$CO, CH=CH wherein R$_B{}^1$ is hydrogen, C$_1$–C$_6$alkyl, aryl, aryl-C$_1$–C$_6$-alkyl, C$_1$–C$_6$alkanoyl, or aroyl, and $R_C{}^1$ is hydrogen, or $C_1$–$C_6$alkyl;

aryl;

substituted aryl wherein the substituent is $C_1$–$C_6$alkyl, amino-$C_1$–$C_6$-alkyl, $C_1$–$C_6$alkoxy, aryloxy, aroyl, hydroxy, halo, or dihalo;

aryl-$C_1$–$C_6$alkyl or heteroaryl-$C_1$–$C_6$-alkyl which include branched $C_1$–$C_6$alkyl groups;

substituted aryl-$C_1$–$C_6$alkyl or substituted heteroaryl-$C_1$–$C_6$alkyl which include branched $C_1$–$C_6$alkyl groups wherein the alkyl groups can be substituted by amino, $C_1$–$C_6$alkanoylamino, aroylamino, or hydroxyl and the aryl and heteroaryl groups can be substituted by halo, dihalo, $C_1$–$C_6$alkyl, hydroxy, $C_1$–$C_6$alkoxy, aryloxy, aroyl, arylthio, amino, amino-$C_1$–$C_6$-alkyl, $C_1$–$C_6$alkanoylamino, aroylamino, di-$C_1$–$C_6$-alkylamino, $C_1$–$C_6$alkylamino, hydroxy-$C_1$–$C_6$-alkyl, trihalo-$C_1$–$C_6$-alkyl, nitro, cyano, or sulfonamido;

$R^2$ is hydroxy;

$C_1$–$C_6$alkoxy;

$C_1$–$C_6$alkenyloxy;

aryl-$C_1$–$C_6$-alkoxy;

amino;

$C_1$–$C_6$alkylamino;

di-$C_1$–$C_6$-alkylamino;

aryl-$C_1$–$C_6$alkylamino;

arylamino;

carboxy-$C_1$–$C_6$-alkylamino;

carboxamido-$C_1$–$C_6$-alkylamino;

aryloxy, or mono- or disubstituted aryloxy wherein the substituents are halo;

m is 1–3;

$R^3$ is $C_1$–$C_6$alkyl or substituted $C_1$–$C_6$alkyl wherein the substituents are hydrogen, $C_1$–$C_6$alkyl, or aryl;

$R^4$ is hydroxy;

$C_1$–$C_6$alkanoyloxy;

aryl-$C_1$–$C_6$-alkanoyloxy;

$R^5$ is hydrogen;

halo;

hydroxy;

$C_1$–$C_6$alkyl; or $C_1$–$C_6$alkoxy; and, a pharmaceutically acceptable salt thereof wherein in said $R^1$–$R^5$ groups aryl is a member of the group consisting of phenyl, naphthyl, or biphenyl; and, heteroaryl is a 5- or 6-membered aromatic ring containing from one to three O, N or S heteroatoms and in a member selected from the group consisting pyridyl, thienyl, furyl, imidazolyl, and thiazolyl as well as bicyclic groups in which a heteroaryl ring is fused to a benzene ring, said bicyclic groups being a member selected from the group consisting of indolyl, quinolinyl, isoquinolinyl, benzimidazolyl, benzothiazolyl, and benzthienyl.

2. A compound of the formula:

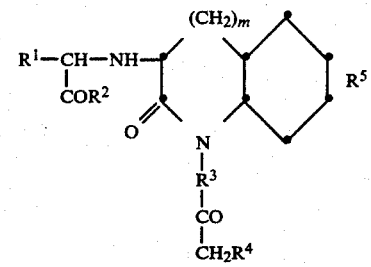

wherein:

$R^1$ is hydrogen;

straight chain or branched, saturated or unsaturated hydrocarbon of 1 to 12 carbon atoms;

$C_3$–$C_{10}$cycloalkyl;

substituted $C_1$–$C_6$alkyl wherein the substituent can be halo, hydroxy, carboxy, $C_1$–$C_6$alkylthio, $C_1$–$C_6$alkoxy, $C_1$–$C_6$alkoxycarbonyl, carboxamido, aryl-$C_1$–$C_6$-alkoxycarbonyl, amino, $C_1$–$C_6$alkylamino, di-$C_1$–$C_6$-alkylamino, $C_1$–$C_6$alkanoylamino, or aroylamino; substituted $C_1$–$C_6$alkyl having the formula $R_A{}^1$(CH$_2$)$_p$—Q—(CH$_2$)$_q$ wherein p is 0–2, q is 1–3, $R_A{}^1$ is aryl or heteroaryl optionally substituted by amino, di-$C_1$–$C_6$-alkylamino, $C_1$–$C_6$alkylamino, hydroxy, hydroxy-$C_1$–$C_6$-alkyl, amino-$C_1$–$C_6$-alkyl, thihalo-$C_1$–$C_6$-alkyl, cyano, nitro, sulfonamido, aroyl, $C_1$–$C_6$alkyl, halo, dihalo, and $C_1$–$C_6$alkoxy, and Q is O, S, N—$R_B{}^1$, CONR$_C{}^1$, NR$_C{}^1$CO, CH=CH wherein $R_B{}^1$ is hydrogen, $C_1$–$C_6$alkyl, aryl, aryl-$C_1$–$C_6$-alkyl, $C_1$–$C_6$alkanoyl, or aroyl, and $R_C{}^1$ is hydrogen, or $C_1$–$C_6$alkyl;

aryl;

substituted aryl wherein the substituent is $C_1$–$C_6$alkyl, amino-$C_1$–$C_6$-alkyl, $C_1$–$C_6$alkoxy, aryloxy, aroyl, hydroxy, halo, or dihalo;

aryl-$C_1$–$C_6$alkyl or heteroaryl-$C_1$–$C_6$-alkyl which include branched $C_1$–$C_6$alkyl groups;

substituted aryl-$C_1$–$C_6$alkyl or substituted heteroaryl-$C_1$–$C_6$alkyl which include branched $C_1$–$C_6$alkyl groups wherein the alkyl groups can be substituted by amino, $C_1$–$C_6$alkanoylamino, aroylamino, or hydroxyl and the aryl and heteroaryl groups can be substituted by halo, dihalo, $C_1$–$C_6$alkyl, hydroxy, $C_1$–$C_6$alkoxy, aryloxy, aroyl, arylthio, amino, amino-$C_1$–$C_6$-alkyl, $C_1$–$C_6$alkanoylamino, aroylamino, di-$C_1$–$C_6$-alkylamino, $C_1$–$C_6$alkylamino, hydroxy-$C_1$–$C_6$-alkyl, trihalo-$C_1$–$C_6$-alkyl, nitro, cyano, or sulfonamido;

$R^2$ is hydroxy;

$C_1$–$C_6$alkoxy;

$C_1$–$C_6$alkenyloxy;

aryl-$C_1$–$C_6$-alkoxy;

amino;

$C_1$–$C_6$alkylamino;

di-$C_1$–$C_6$-alkylamino;

aryl-$C_1$–$C_6$alkylamino;

arylamino;

carboxy-$C_1$–$C_6$-alkylamino;

carboxamido-$C_1$–$C_6$-alkylamino;

aryloxy, or mono- or disubstituted aryloxy wherein the substituents are halo;

m is 1–3;

$R^3$ is $C_1$–$C_6$alkyl or substituted $C_1$–$C_6$alkyl wherein the substituents are hydrogen, $C_1$–$C_6$alkyl, or aryl;

$R^4$ is
hydroxy;
$C_1$–$C_6$alkanoyloxy;
aryl-$C_1$–$C_6$-alkanoyloxy;

$R^5$ is
hydrogen;
halo;
hydroxy;
$C_1$–$C_6$alkyl; or
$C_1$–$C_6$alkoxy; and, a pharmaceutically acceptable salt thereof wherein in said $R^1$–$R^5$ groups aryl is a member of the group consisting of phenyl, naphthyl, or biphenyl; and, heteroaryl is a 5- or 6-membered aromatic ring containing from one to three O, N, or S heteroatoms and is a member selected from the group consisting pyridyl, thienyl, furyl, imidazolyl, and thiazolyl as well as bicyclic groups in which a heteroaryl ring is fused to benzene ring, said bicyclic groups being a member selected from the group consisting of indolyl, quinolinyl, isoquinolinyl, benzimidazolyl, benzothiazolyl, and benzthienyl.

3. A compound which is a member of the group:
1-(3-acetoxy-2-oxopropyl)-3-(1(S)-carboethoxy-3-phenyl-1-propyl)-(S)-aminohomodihydrocarbostyril;
1-(3-hydroxy-2-oxopropyl)-3-(1(S)-carboethoxy-3-phenyl-1-propyl)-(S)-aminohomodihydrocarbostyril; and,
1-(3-hydroy-2-oxopropyl)-3-(1(S)-carboxy-3-phenylpropyl)-(S)-aminohomodihydrocarbostyril.

* * * * *

UNITED STATES PATENT AND TRADEMARK OFFICE
CERTIFICATE OF CORRECTION

PATENT NO. : 4,652,641

DATED : March 24, 1987

INVENTOR(S) : William H. Parsons

It is certified that error appears in the above-identified patent and that said Letters Patent is hereby corrected as shown below:

On the Title Page, Item [73] should read

-- [73] Assignee: Merck & Co., Inc., Rahway, N. J. --.

Signed and Sealed this

Fifth Day of January, 1988

Attest:

DONALD J. QUIGG

*Attesting Officer*  *Commissioner of Patents and Trademarks*